(12) United States Patent
Bossi et al.

(10) Patent No.: US 8,359,924 B1
(45) Date of Patent: Jan. 29, 2013

(54) BOND INTERFACE TESTING (75) Inventors: Richard Henry Bossi, Renton, WA (US); Kevin R. Housen, Tacoma, WA (US)

(73) Assignee: The Boeing Company, Chicago, IL (US)

( * ) Notice: Subject to any disclaimer, the term of this patent is extended or adjusted under 35 U.S.C. 154(b) by 302 days.

(21) Appl. No.: 12/828,519

(22) Filed: Jul. 1, 2010

(51) Int. Cl.
*G01N 29/04* (2006.01)

(52) U.S. Cl. .................. 73/588; 73/597; 73/602

(58) Field of Classification Search ............ 73/582, 73/588, 611–612, 614–617, 589, 602, 597–598, 73/827
See application file for complete search history.

(56) References Cited

U.S. PATENT DOCUMENTS

| | | | |
|---|---|---|---|
| 3,813,926 A * | 6/1974 | Stubbeman | 73/609 |
| 4,004,456 A | 1/1977 | Vahaviolos | |
| 4,184,373 A * | 1/1980 | Evans et al. | 73/588 |
| 4,207,771 A | 6/1980 | Carlos et al. | |
| 4,210,028 A * | 7/1980 | Hildebrand | 73/598 |
| 4,401,477 A | 8/1983 | Clauer et al. | |
| 4,545,018 A | 10/1985 | Clements et al. | |
| 4,824,250 A | 4/1989 | Newman | |
| 4,838,085 A | 6/1989 | Pellerin et al. | |
| 4,901,357 A | 2/1990 | Albright | |
| 5,127,019 A | 6/1992 | Epstein et al. | |
| 5,201,225 A * | 4/1993 | Takahashi et al. | 73/615 |
| 5,269,778 A | 12/1993 | Rink et al. | |
| 5,473,315 A | 12/1995 | Holroyd | |
| 5,572,016 A | 11/1996 | Wood et al. | |
| 5,729,012 A | 3/1998 | Wood et al. | |
| 5,803,965 A | 9/1998 | Yoon | |
| 5,965,877 A | 10/1999 | Wood et al. | |
| 6,008,887 A | 12/1999 | Klein et al. | |
| 6,070,466 A * | 6/2000 | Taran et al. | 73/622 |
| 6,238,187 B1 | 5/2001 | Dulaney et al. | |
| 6,282,964 B1 | 9/2001 | Hancock et al. | |
| 6,288,358 B1 | 9/2001 | Dulaney et al. | |
| 6,373,876 B1 | 4/2002 | Dulaney et al. | |
| 6,479,790 B1 | 11/2002 | Graham et al. | |

(Continued)

FOREIGN PATENT DOCUMENTS

GB    2225427 A    5/1990

OTHER PUBLICATIONS

Gupta et al., "Nanosecond Rise-time Stress Pulses Using Lasers for Applications to Material Characterization", AMD-vol. 165, Experimental Techniques in the Dynamics of Deformable Solids, ASME 1993, pp. 61-70.

(Continued)

*Primary Examiner* — Helen C. Kwok
(74) *Attorney, Agent, or Firm* — Yee & Associates, P.C.

(57) ABSTRACT

A method and apparatus for testing a bond interface is provided. An initial wave is transmitted into a first end of a first material. The first material is connected to a second material by an adhesive at a bond interface. The first material is dissimilar to the second material. The initial wave splits into a first wave and a second wave at the bond interface. Parameters are changed so a first wave travels through the first material to the first end of the first material and back to the bond interface in a first amount of time and the second wave travels through the second material to a second end of the second material and back to the bond interface in a second amount of time. The first amount of time is substantially equal to the second amount of time. A tension is obtained in the adhesive at the bond interface.

20 Claims, 5 Drawing Sheets

U.S. PATENT DOCUMENTS

| | | |
|---|---|---|
| 6,512,584 B1 | 1/2003 | O'Loughlin et al. |
| 6,554,921 B2 | 4/2003 | Sokol et al. |
| 6,622,568 B2 | 9/2003 | Nelson et al. |
| 6,657,160 B2 | 12/2003 | Hackel et al. |
| 6,759,626 B2 | 7/2004 | Clauer et al. |
| 6,848,321 B2 | 2/2005 | Bossi et al. |
| 6,912,906 B2 * | 7/2005 | Farassat ............... 73/588 |
| 6,945,114 B2 | 9/2005 | Kenderian et al. |
| 7,131,331 B2 | 11/2006 | Bates |
| 7,150,193 B2 | 12/2006 | Lorraine et al. |
| 7,154,067 B2 | 12/2006 | Yoshii |
| 7,253,908 B2 | 8/2007 | Vaccaro et al. |
| 7,270,004 B2 | 9/2007 | Dickinson et al. |
| 7,341,758 B2 * | 3/2008 | Stewart et al. ............ 427/8 |
| 7,507,312 B2 * | 3/2009 | Bossi et al. ............ 156/714 |
| 7,509,876 B1 * | 3/2009 | Sokol et al. ............ 73/827 |
| 7,584,062 B1 * | 9/2009 | Tat et al. ............ 702/39 |
| 7,735,377 B1 | 6/2010 | Sokol et al. |
| 2004/0224179 A1 | 11/2004 | Sokol et al. |
| 2005/0120803 A1 | 6/2005 | Sokol et al. |
| 2008/0257048 A1 | 10/2008 | Walters et al. |

OTHER PUBLICATIONS

Yuan et al., "Measurement of Interface Strength byt eh Modified Laser Spallation Technique", 1993, Journal of Applied Physics, 74(4) pp. 2388-2410.

Boustie et al., "Laser Shock Waves: fundamentals and applications", 1st International Symposium on Laser Ultrasonics: Science, Technology and Applications, Jul. 2008, Montreal Canada, pp. 1-12.

Bossi et al., "Application of Stress Waves to Bond Inspection", SAMPE 2004, Long Beach CA, May 2004, pp. 1-14.

Bossi et al., "Using Shock Loads to Measure Bonded Joint Strength", Materials Evaluation, 60, 11, 2002, pp. 1-14.

Bossi et al., "Laser Bond Inspection Device for Composites: Has the Holy Grail Been Found?", Nondestructive Testing Information Analysis Center Newsletter, vol. 30, No. 2, 2005, pp. 1-8.

Bossi et al., "Laser Bond Inspection", Materials Evaluation, Laser Bond Testing, vol. 67, No. 7 Jul. 2009, pp. 1-18.

* cited by examiner

BOND INTERFACE TESTING

BACKGROUND INFORMATION

1. Field

The present disclosure relates generally to strength measurement of materials. More particularly, the invention relates to a non-destructive method and apparatus for measuring the strength of a bond interface between bonded structures.

2. Background

Bonded joints are widely used in a variety of structural applications, and more specifically, primary composite structures are often bonded together in select aerospace applications. The strength of the bonded joint between composite structures needs to be certifiable if the bonded joint is used in a primary structure application. Conventional measurement of bond strength generally involves static proof testing. For the structure to be used in aerospace service, structural proof testing can be performed to the limit load. Limit load is the maximum load that a structure is expected to see in service. However, the cost of such testing is usually high. Physical testing to failure to validate strength is more commonly performed using witness coupons. The witness coupons are samples that are assembled at the same time as the bonded joint using the same materials and following as closely as possible the bonding process of the real structure. The coupons are then tested to failure to validate the process quality. While useful as an indicator, these test articles are not a part of the vehicle structure.

Non-destructive testing methods exist for composite structures; however, the non-destructive methods generally detect the presence of a defect such as a void or unbond with in a joint not the strength thereof. Such methods may include, for example, ultrasonics, x-rays, and acoustics, among others commonly known in the art.

Laser bond inspection is a method of testing bonds using stress waves. The method involves depositing laser energy onto the front surface of a bonded article and generating compression stress waves that reflect off of the back surface of the bonded article as tensile stress waves. The tensile waves predominantly provide the stresses that test the bond between similar materials. If a tensile wave of sufficient strength encounters a weak bond, the bond will separate. A tensile wave is a wave that causes tension in a material. Unfortunately, when the bond is between dissimilar materials the wave reflected from the back surface may not create sufficient tension to evaluate the strength of the bond.

The features, functions, and advantages can be achieved independently in various embodiments of the present disclosure or may be combined in yet other embodiments in which further details can be seen with reference to the following description and drawings.

SUMMARY

In one advantageous embodiment, a method is present for testing a bond interface. The method comprises transmitting an initial wave into a first end of a first material. The first material is connected to a second material by an adhesive at a bond interface. When the materials are dissimilar, the initial wave splits into a first wave and a second wave at the location. The method also changes parameters as needed by means of timing delay lines such that a first wave travels through the first material to the first end of the first material and back to the bond interface in a first amount of time and the second wave travels through the second material to a second end of the second material and back to the bond interface in a second amount of time. The first amount of time is substantially equal to the second amount of time peaking the tension at the bond. A tension is obtained in the adhesive at the bond interface.

In another advantageous embodiment, a method is present for testing a bond interface. The method comprises transmitting an initial wave into a first end of a first material. The first material is connected to a second material by an adhesive at a bond interface. The initial wave splits into a first wave and a second wave at the bond interface. The method also comprises transmitting a second initial wave into a second end of the second material. The first material is dissimilar to the second material and of lower acoustic impedance. The second initial wave splits into a third wave and a fourth wave at the bond interface. The method also comprises changing parameters such that a first wave travels through the first material to the first end of the first material and back to the bond interface in a first amount of time. The fourth wave travels through the first material and reflects back to the interface in a fourth amount of time. The first amount of time is substantially equal to the fourth amount of time enhancing the tension at the bond interface. A tension is obtained in the adhesive at the bond interface.

In yet another advantageous embodiment, an apparatus comprises a number of lasers configured to generate a number of waves and a controller associated with the number of lasers. The controller is configured to transmit the wave into a first end of the first material. The bond interface is where the adhesive bonds the first material to a second material. The first material is dissimilar to the second material. The initial waves from each laser split into multiple waves. The waves travel through each material. By proper controller and delay line timing, a tension wave may be peaked at the bond interface. A tension is obtained in the adhesive at the bond interface.

Therefore, it would be advantageous to have a method and apparatus which takes into account one or more of the issues discussed above, as well as possibly other issues.

BRIEF DESCRIPTION OF THE DRAWINGS

The novel features believed characteristic of the advantageous embodiments are set forth in the appended claims. The advantageous embodiments, however, as well as a preferred mode of use, further objectives and advantages thereof, will best be understood by reference to the following detailed description of an advantageous embodiment of the present disclosure when read in conjunction with the accompanying drawings, wherein:

DETAILED DESCRIPTION

Figures 1, 2:
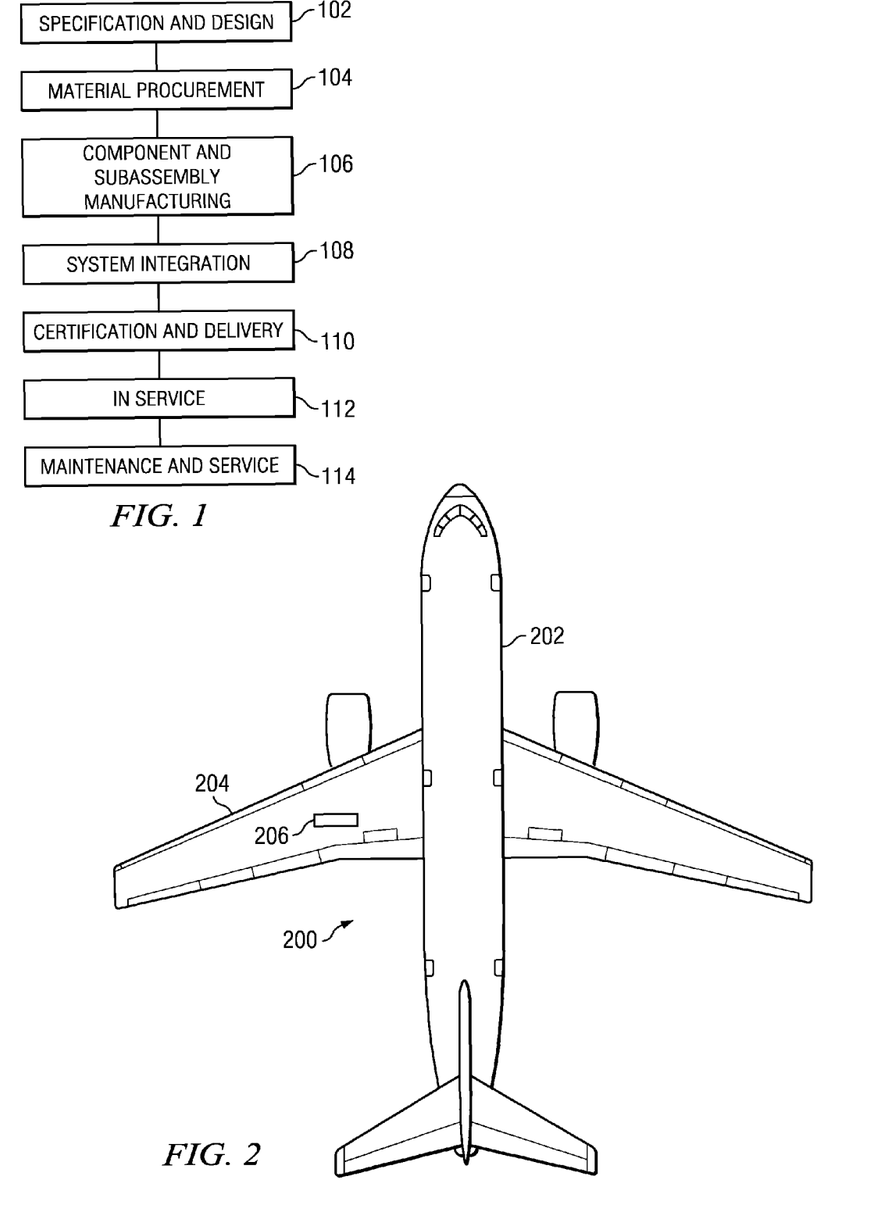
FIG. 1 is an illustration of an aircraft manufacturing and service method in accordance with an advantageous embodiment.
FIG. 2 is an illustration of an aircraft in which an advantageous embodiment may be implemented.

Referring more particularly to the drawings, embodiments of the disclosure may be described in the context of aircraft manufacturing and service method 100 as shown in FIG. 1 and aircraft 200 as shown in FIG. 2. Turning first to FIG. 1, a diagram illustrating an aircraft manufacturing and service method is depicted in accordance with an advantageous embodiment. During pre-production, exemplary aircraft manufacturing and service method 100 may include specification and design 102 of aircraft 200 in FIG. 2 and material procurement 104.

During production, component and subassembly manufacturing 106 and system integration 108 of aircraft 200 in FIG. 2 takes place. Thereafter, aircraft 200 in FIG. 2 may go through certification and delivery 110 in order to be placed in service 112. While in service by a customer, aircraft 200 in FIG. 2 is scheduled for routine maintenance and service 114, which may include modification, reconfiguration, refurbishment, and other maintenance or service.

Each of the processes of aircraft manufacturing and service method 100 may be performed or carried out by a system integrator, a third party, and/or an operator. In these examples, the operator may be a customer. For the purposes of this description, a system integrator may include, without limitation, any number of aircraft manufacturers and major-system subcontractors; a third party may include, without limitation, any number of vendors, subcontractors, and suppliers; and an operator may be an airline, leasing company, military entity, service organization, and so on.

Apparatus and methods embodied herein may be employed during any one or more of the stages of aircraft manufacturing and service method 100 in FIG. 1. For example, components or subassemblies produced in component and subassembly manufacturing 106 in FIG. 1 may be fabricated or manufactured in a manner similar to components or subassemblies produced while aircraft 200 is in service 112 in FIG. 1.

Turning now to FIG. 2, a diagram illustrating an aircraft is depicted in accordance with an advantageous embodiment. In this example, aircraft 200 is produced by aircraft manufacturing and service method 100 in FIG. 1 and may include airframe 202 with wing 204. Aircraft 200 may have composite 206 to metal bonds in wing 204 of aircraft 200. Composite 206 to metal bonds in the wing 204 increase the strength of a portion of wing 204. Although an aerospace example is shown, different advantageous embodiments may be applied to other industries, such as the automotive industry.

Also, one or more apparatus embodiments, method embodiments, or a combination thereof may be utilized during production stages, such as component and subassembly manufacturing 106 and system integration 108 in FIG. 1, for example, without limitation, by substantially expediting the assembly of or reducing the cost of aircraft 200. Similarly, one or more of apparatus embodiments, method embodiments, or a combination thereof may be utilized while aircraft 200 is in service 112 or during maintenance and service 114 in FIG. 1.

As another example, one or more of the different advantageous embodiments may be used to manufacture parts for use in aircraft 200 during component and subassembly manufacturing 106 and/or maintenance and service 114.

Figure 3:
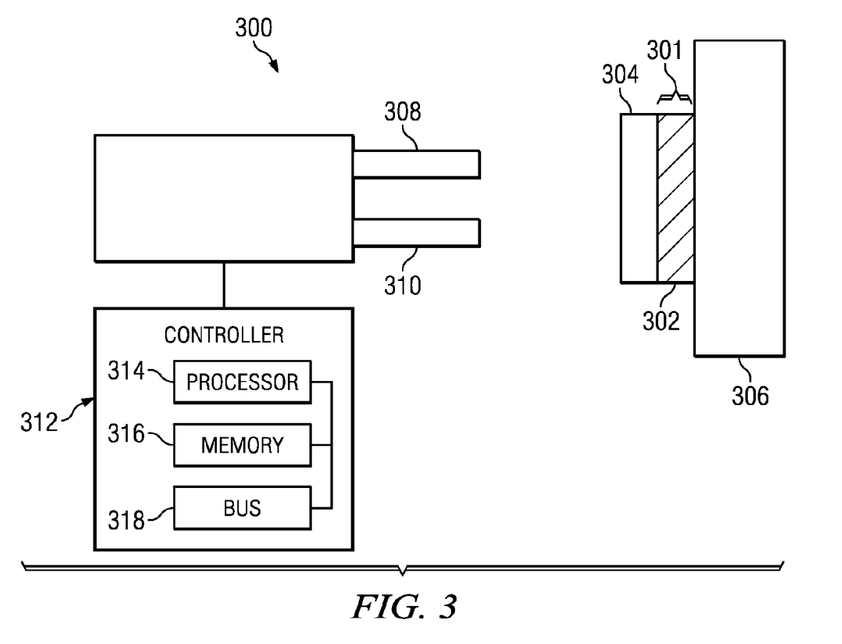
FIG. 3 is a diagram illustrating a strength test environment in accordance with an advantageous embodiment.

Turning now to FIG. 3, a diagram illustrating a strength test environment is depicted in accordance with an advantageous embodiment. Strength test environment 300 may be implemented during component and subassembly manufacturing 106 and/or maintenance and service 114 as shown in FIG. 1. Strength test environment 300 may implemented on aircraft 200 as shown in FIG. 2. Strength test environment 300 may be an environment in which the strength of a bond interface of materials may be tested. For example, strength test environment 300 may be an environment in which the strength of bond interface 301 may be tested.

Adhesive 302 may be comprised of film or paste epoxy. Epoxy is a polymer formed from a reaction of a resin and a hardener. Adhesive 302 may be used to bond together two materials, such as, for example, material 304 and material 306. It is noted that the depicted size of adhesive 302 relative to materials 304 and 306 may not be indicative of the actual size used in practice. Adhesive 302 may be smaller than the ratios as depicted.

Materials 304 and 306 may be any type of material. For example, materials 304 and 306 may both be composite materials. In other illustrative embodiments, material 304 may be a composite while material 306 may be a metal, such as titanium.

Bond interface 301 is the location where materials 304 and 306 are joined together by either a fastener or adhesive, such as adhesive 302. To test the strength of bond interface 301, laser 308 may transmit a wave into material 304, adhesive 302, and material 306. Laser 308 may be any laser configured to produce waves in adhesive 302, material 304, and material 306.

The waves produce vibrations in materials 304 and 306. Laser 310 may be used to measure any produced vibrations. The vibrations may be used to identify a failure of bond interface 301. In different illustrative embodiments, other methods may be used to identify a failure of bond interface 301. For example, ultrasonics, x-rays, and acoustics, among other non-destructive test methods.

Controller 312 is used to control lasers 308 and 310. Controller 312 may be any type of microcontroller or controller. Controller 312 comprises processor 314, memory 316, and bus 318. Processor 314 serves to execute instructions for software that may be loaded into memory 316. Processor 314 may be a number of processors, a processor unit, a multiprocessor core, or some other type of processor, depending on the particular implementation. A number, as used herein with reference to an item, means one or more items. Further, processor 314 may be implemented using a number of heterogeneous processor systems in which a main processor is present with secondary processors on a single chip. As another illustrative example, processor 314 may be a symmetric multiprocessor system containing multiple processors of the same type.

Memory 316 is an example of a storage device. A storage device is any piece of hardware that is capable of storing information, such as, for example, without limitation, data, program code in functional form, and/or other suitable information either on a temporary basis and/or a permanent basis. Memory 316, in these examples, may be, for example, a random access memory or any other suitable volatile or non-volatile storage device.

Bus 318 may be a subsystem that transfers data between computer components. For example, bus 318 may be used to transfer data from processor 314 to memory 316.

The different advantageous embodiments recognize and take into account a number of considerations. For example, the different advantageous embodiments recognize and take into account that current non-destructive testing methods exist for composite structures; however, the non-destructive methods generally detect the presence of a defect, such as a voids or foreign objects within a bond, not the strength thereof. Such methods may include, for example, ultrasonics, x-rays, and acoustics, among others commonly known in the art.

Laser bond inspection is a method of wave testing bonds which involves depositing laser energy onto the front surface of a bonded article and generating compression waves that reflect off of the back surface of the bonded article as tensile waves. The tensile waves predominantly provide the stresses that test the bond between similar materials. If a tensile wave of sufficient strength encounters a weak bond, the bond will fail.

A special application of wave testing is for bonds between dissimilar materials. Dissimilar materials have different acoustic impedances. In this case, the above-mentioned process will not apply due to the impedance mismatch and reflections of the waves at the bond interface. To develop sufficient tension loads from waves in dissimilar material bonds, special consideration must be developed as described in the present disclosure. Once the laser bond inspection is performed, then a non-destructive process may be used to determine whether the bond failed.

Further, the different advantageous embodiments also recognize that current laser bond inspection may not have enough energy in the generated waves to test a bond interface when using dissimilar materials. When waves are split at the bond interface they travel to the end of the two materials and then back to the adhesive as tensile waves. The tensile waves separately may not provide enough energy to test the bond interface.

A method and apparatus for testing a bond interface is provided. An initial wave is transmitted into a first end of a first material. The first material is connected to a second material by an adhesive at a bond interface. The first material is dissimilar to the second material. The initial wave splits into a first wave and a second wave at the location. Parameters are changed such that a first wave travels through the first material to the first end of the first material and back to the bond interface in a first amount of time and the second wave travels through the second material to a second end of the second material and back to the bond interface in a second amount of time. The first amount of time is adjusted by parameter to be substantially equal to the second amount of time. A tension is obtained in the adhesive at the bond interface.

Figure 4:
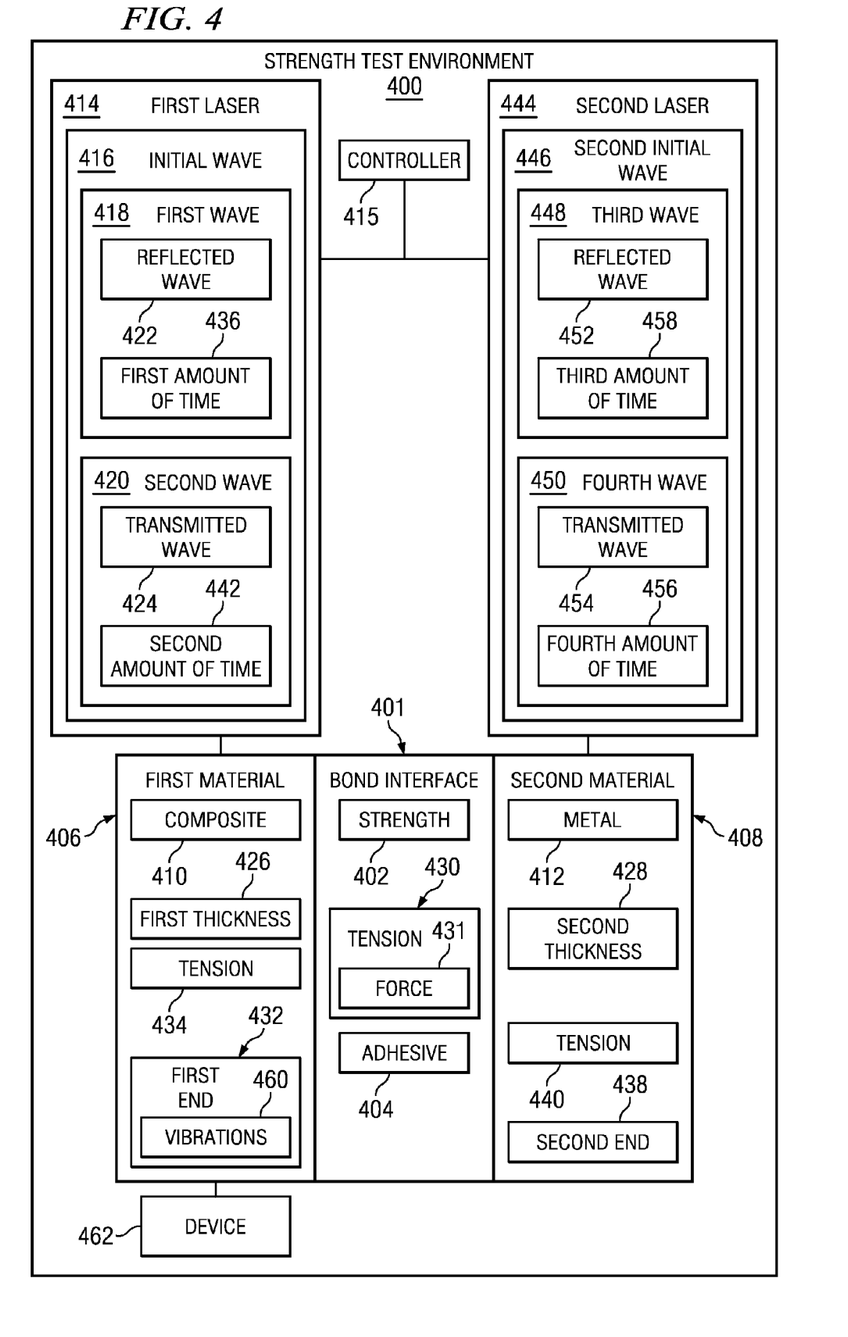
FIG. 4 is a block diagram illustrating a strength test environment in accordance with an advantageous embodiment.

With reference to FIG. 4, a block diagram illustrating a strength test environment is depicted in accordance with an advantageous embodiment. Strength test environment 400 may be one example of one implementation of strength test environment 300 as shown in FIG. 3. Strength test environment 400 may be an environment in which the strength of materials may be tested. For example, strength test environment 400 may be an environment in which strength 402 of bond interface 401 may be tested.

Adhesive 404 may be comprised of film or paste epoxy. Epoxy is a polymer formed from a reaction of a resin and a hardener. Adhesive 404 may be used to bond together two materials, such as, for example, first material 406 and second material 408.

First material 406 and second material 408 may be any type of material. In an advantageous embodiment, first material 406 and second material 408 are dissimilar materials. Dissimilar means the materials may have different densities and/or different acoustic impedances. In different illustrative embodiments, first material 406 may be composite 410, such as a graphite epoxy composite. In different illustrative examples, second material 408 may be metal 412, such as titanium, aluminum, and/or steel.

To test strength 402 of bond interface 401, first laser 414 may transmit initial wave 416 into first material 406. First laser 414 may be any laser configured to produce waves in adhesive 404, first material 406, and second material 408.

Controller 415 may be used to control first laser 414. Controller 415 may be one example of one implementation of controller 312 of FIG. 3. Controller 415 may control laser 414 to transmit a wave.

Initial wave 416 may be transmitted into first material 406. When initial wave 416 reaches bond interface 401, some of initial wave 416 reflects and some of initial wave 416 transmits. Initial wave 416 separates into first wave 418 and second wave 420. First wave 418 may be reflected wave 422. Second wave 420 may be transmitted wave 424. Reflected wave 422 is the part of initial wave 416 that is reflected back through first material 406. Transmitted wave 424 is the part of initial wave 416 that is transmitted through bond interface 401 to second material 408.

When materials are similar, substantially all energy of initial wave 416 will be transmitted through to second material 408. For example, when both first material 406 and second material 408 are similar composite materials, transmitted wave 424 may be larger than if first material 406 and second material 408 were different materials.

When materials are similar, substantially all of initial wave 416 will be transmitted through a bond interface to form transmitted wave 424. Transmitted wave 424 may be of proper strength to test strength 402 of bond interface 401. When first material 406 and second material 408 are of dissimilar materials, such as composite 410 and metal 412, the two resulting waves may not have enough strength to test strength 402 of bond interface 401.

In one or more advantageous embodiments, first thickness 426 of first material 406 and second thickness 428 of second material 408 are selected to create tension 430 in adhesive 404 to test bond interface 401. Tension 430 may be created from the timing combination of reflected wave 422 and transmitted wave 424. Tension 430 is force 431 related to the stretching of an object. Tension 430 would be the opposite of compression. A reflected wave is the part of an initial wave that is reflected back through a material at the intersection of a dissimilar material.

Reflected wave 422 travels from bond interface 401 to first end 432 of first material 406 then back to bond interface 401. When traveling from bond interface 401 to first end 432 of first material 406, reflected wave 422 causes compression in first material 406. When traveling from first end 432 of first material 406 to bond interface 401, reflected wave 422 causes tension 434 in first material 406. The time it takes for reflected wave 422 to travel from bond interface 401 to first end 432 of first material 406 and back to bond interface 401 is first amount of time 436.

Transmitted wave 424 travels from bond interface 401 to second end 438 of second material 408 then back to bond interface 401. When traveling from adhesive 404 to second end 438 of second material 408, transmitted wave 424 causes compression in second material 408. When traveling from second end 438 of second material 408 to adhesive 404, transmitted wave 424 causes tension 440 in second material 408. The time it takes for transmitted wave 424 to travel from bond interface 401 to second end 438 of second material 408 and back to bond interface 401 is second amount of time 442.

In one or more advantageous embodiments, first thickness 426 of first material 406 and second thickness 428 of second material 408 are selected to allow for first amount of time 436 and second amount of time 442 to be substantially the same.

When the two times are the same, tension 430 is generated to allow for a test of bond interface 403.

In different illustrative embodiments, delay lines are added to allow first amount of time 436 and second amount of time 442 to be substantially the same without changing first thickness 426 or second thickness 428. A delay line is a device which allows the time delay of a wave or signal. A delay line may be used to allow for reflected wave 422 and transmitted wave 424 to meet at adhesive bond at the same time instead of adjusting first thickness 426 and second thickness 428.

In different advantageous embodiments, instead of changing first thickness 426, second thickness 428, or adding delay lines to allow for reflected wave 422 and transmitted wave 424 to combine, second laser 444 is used to provide second initial wave 446. Second initial wave 446 is transmitted into second material 408. Second initial wave 446 separates at bond interface 401 into third wave 448 and fourth wave 450.

Third wave 448 is reflected wave 452. Fourth wave 450 may be transmitted wave 454. Reflected wave 452 is the part of second initial wave 446 that is reflected back through second material 408. Transmitted wave 454 is the part of second initial wave 446 that is transmitted through bond interface 401 to first material 406.

Second initial wave 446 may be timed so that second initial wave 446 reaches bond interface 401 at substantially the same time as initial wave 416. When initial wave 416 and second initial wave 446 reach bond interface 401 at the same time, both waves separate at the same time. When separation occurs concurrently for both waves, the resulting separated waves may have similar propagation times.

For example, reflected wave 422 and transmitted wave 454 may have similar travel times. Therefore, first amount of time 436 may be substantially similar to fourth amount of time 456. When using second laser 444, tension 430 may be obtained with another combination of waves. Controller 415 may also control second laser 444.

When tension 430 causes failure of the bond, vibrations 460 that may be measured from either the first material 406 or the second material 408 surfaces will be substantially different than if no failure occurs. To measure vibrations 460, device 462 is positioned to take readings of vibrations 460 coming from first end 432 of first material 406. Device 462 may be a type of laser configured to measure vibrations. In different embodiments, measurements may be taken by some other method or in a different location, such as on second material 408.

Figure 5:
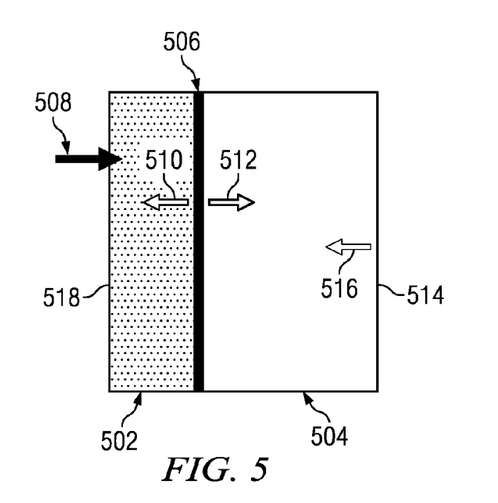
FIG. 5 is a diagram illustrating a first and second material in accordance with an advantageous embodiment.

Turning to FIG. 5, a diagram illustrating a first and second material is depicted in accordance with an advantageous embodiment. First material 502 may be one example of one implementation of first material 406 of FIG. 4. Second material 504 may be one example of one implementation of second material 408 of FIG. 4.

First material 502 and second material 504 may be bonded together at bond interface 506. Initial wave 508 may be transmitted into first material 502. Initial wave 508 may be one example of one implementation of initial wave 416 as shown in FIG. 4. Initial wave 508 separates into reflected wave 510 and transmitted wave 512 at bond interface 506. Once transmitted wave 512 reaches end 514, it heads back towards bond interface 506 as transmitted wave 516. Likewise, reflected wave 510 heads back towards bond interface 506 once reflected wave 510 reaches end 518.

Figure 6:
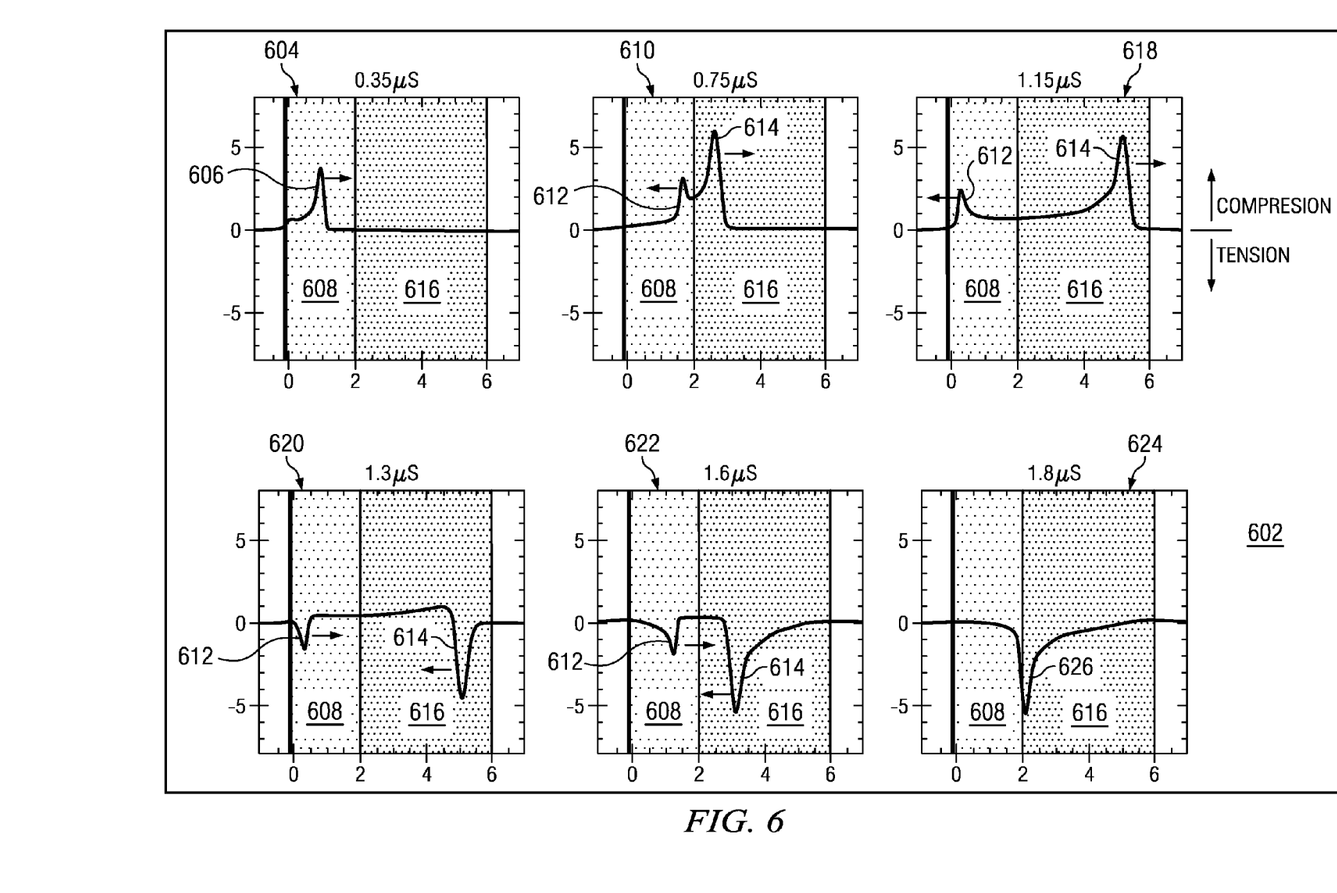
FIG. 6 is a series of diagrams in accordance with an advantageous embodiment.

Turning to FIG. 6, a series of diagrams is depicted in accordance with an advantageous embodiment. Diagrams 602 illustrate one example of an initial wave as it travels through a first material and separates into a reflected wave and transmitted wave at a bond interface.

In diagram 604, at about 0.35 microseconds, initial wave 606 is traveling through first material 608. In diagram 610, at about 0.75 microseconds, initial wave 606 has reached the location between first material 608 and second material 616 and separated into reflected wave 612 and transmitted wave 614.

In diagram 618, at about 1.15 microseconds, reflected wave 612 has almost reached the end of first material 608 and transmitted wave 614 has almost reached the end of second material 616. In diagram 620, at about 1.3 microseconds, both reflected wave 612 and transmitted wave 614 are now tensile waves and are both traveling back towards the intersection of first material 608 and second material 616.

In diagram 622, at about 1.6 microseconds, both reflected wave 612 and transmitted wave 614 are still traveling towards the intersection of first material 608 and second material 616. In diagram 624, at about 1.8 microseconds, both reflected wave 612 and transmitted wave 614 are now at the intersection of first material 608 and second material 616. Reflected wave 612 and transmitted wave 614 have combined to form tension 626 on any adhesive that may be bonding first material 608 and second material 616.

Figure 7:
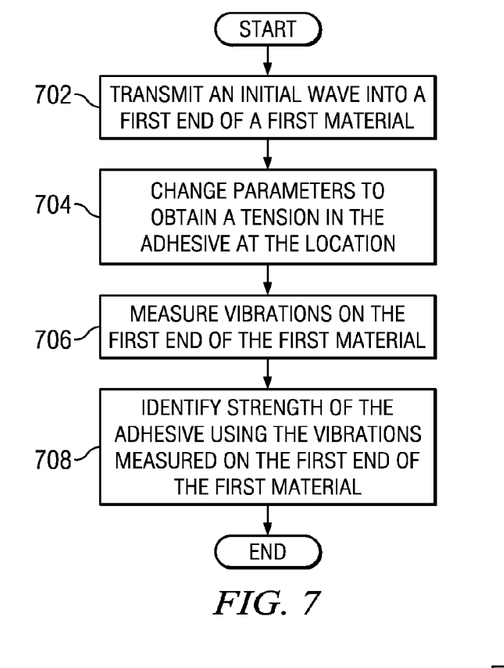
FIG. 7 is a flowchart for a process for testing bond interface strength in accordance with an advantageous embodiment.

With reference now to FIG. 7, a process for testing bond interface strength is depicted in accordance with an advantageous embodiment. The process may be implemented by strength test environment 400 as shown in FIG. 4.

The process begins by transmitting an initial wave into a first end of a first material (operation 702). The first material is connected to a second material by an adhesive at a bond interface. The initial wave splits into a first wave and a second wave at the location. The process then changes parameters to obtain a tension in the adhesive at the bond interface (operation 704). Changing parameters may comprise selecting a first thickness of the first material and a second thickness of the second material where the first amount of time is substantially equal to the second amount of time. In different advantageous embodiments, changing parameters may also comprise adding delay lines to where the first amount of time is substantially equal to the second amount of time.

The first wave travels through the first material to the first end of the first material and back to the bond interface in a first amount of time and the second wave travels through the second material to a second end of the second material and back to the bond interface in a second amount of time. The first amount of time is substantially equal to the second amount of time.

The process measures the vibrations on the first end of the first material (operation 706). The process then identifies strength of the bond interface using the vibrations measured on the first end of the first material (operation 708). The strength of the bond interface may be determined by identifying whether the bond failed. The process terminates thereafter.

Figure 8:
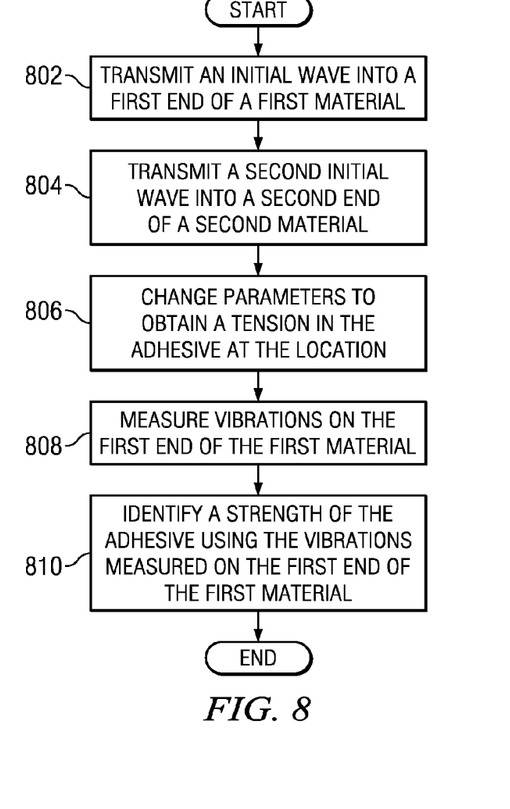
FIG. 8 is a flowchart for an additional process for testing bond interface strength in accordance with an advantageous embodiment.

With reference now to FIG. 8, an additional process for testing bond interface strength is depicted in accordance with an advantageous embodiment. The process may be implemented by strength test environment 400 as shown in FIG. 4.

The process begins by transmitting an initial wave into a first end of a first material (operation 802). The first material is connected to a second material by an adhesive at a bond interface. The initial wave splits into a first wave and a second wave at the bond interface. The process then transmits a second initial wave into a second end of the second material (operation 804). The second initial wave splits into a third wave and a fourth wave at the bond interface.

The process then changes parameters of the controller to obtain a tension in the adhesive at the bond interface (operation 806). Changing parameters may comprise adjusting the controller to transmit the initial wave and the second initial wave to where the first amount of time is substantially equal to the fourth amount of time.

The first wave travels through the first material to the first end of the first material and back to the bond interface in a first amount of time. The fourth wave travels through the first material in a fourth amount of time. The first amount of time is substantially equal to the fourth amount of time.

Additionally, the second wave and third wave will also travel together. Therefore, the second amount of time and third amount of time may be substantially similar.

The process then measures vibrations on the first end of the first material (operation 808). The process identifies strength of the bond interface using the vibrations measured on the first end of the first material (operation 810). The strength of the bond interface may be determined by identifying whether the bond failed. The process terminates thereafter.

The flowchart and block diagrams in the different depicted embodiments illustrate the architecture, functionality, and operation of some possible implementations of apparatus and methods in different advantageous embodiments. In this regard, each block in the flowchart or block diagrams may represent a module, segment, function, and/or portion of an operation or step.

In some alternative implementations, the function or functions noted in the block may occur out of the order noted in the figures. For example, in some cases, two blocks shown in succession may be executed substantially concurrently, or the blocks may sometimes be executed in the reverse order, depending upon the functionality involved. Also, other blocks may be added in addition to the illustrated blocks in a flowchart or block diagram. For example, in different advantageous embodiments, operation 802 and operation 804 may be performed at the same time.

A method and apparatus for testing bond interface strength is provided. An initial wave is transmitted into a first end of a first material. The first material is connected to a second material by an adhesive at a bond interface. The first material is dissimilar to the second material. The initial wave splits into a first wave and a second wave at the location. Parameters are changed such that a first wave travels through the first material to the first end of the first material and back to the bond interface in a first amount of time and the second wave travels through the second material to a second end of the second material and back to the bond interface in a second amount of time. The first amount of time is substantially equal to the second amount of time. A tension is obtained in the adhesive at the bond interface. In other advantageous embodiments the change of parameters 806 may be performed before operations 802 and 804.

The different illustrative embodiments provide a bond interface strength test for bonds between different materials. The test provides for waves input into the materials to create a tension significant enough at the bond interface to fail a weak bond. The waves are timed by selecting different thicknesses to the materials, adding delay lines, and/or using two lasers.

The description of the different advantageous embodiments has been presented for purposes of illustration and description, and is not intended to be exhaustive or limited to the embodiments in the form disclosed. Many modifications and variations will be apparent to those of ordinary skill in the art. Further, different advantageous embodiments may provide different advantages as compared to other advantageous embodiments. The embodiment or embodiments selected are chosen and described in order to best explain the principles of the embodiments, the practical application, and to enable others of ordinary skill in the art to understand the disclosure for various embodiments with various modifications as are suited to the particular use contemplated.

Although the different advantageous embodiments have been described with respect to parts for aircraft, other advantageous embodiments may be applied to parts for other types of adhesive and bonding strength test environments. For example, without limitation, other advantageous embodiments may be applied to bonds for spacecraft and/or any type of object where two materials are bonded together by an adhesive.

Further, different advantageous embodiments may provide different advantages as compared to other advantageous embodiments. The embodiment or embodiments selected are chosen and described in order to best explain the principles of the embodiments, the practical application, and to enable others of ordinary skill in the art to understand the disclosure for various embodiments with various modifications as are suited to the particular use contemplated.

What is claimed is:

1. A method for testing a bond interface, the method comprising:
    transmitting an initial wave into a first end of a first material connected to a second material by an adhesive at a bond interface such that the initial wave splits into a first wave and a second wave at the bond interface, and wherein the first material is dissimilar to the second material; and
    causing the first wave to travel through the first material to the first end of the first material and back to the bond interface in a first amount of time and the second wave to travel through the second material to a second end of the second material and back to the bond interface in a second amount of time, such that the first amount of time is substantially equal to the second amount of time, wherein a tension is obtained in the adhesive at the bond interface.

2. The method of claim 1, further comprising:
    repeatedly transmitting additional waves into the first material to generate vibrations in the first material and the second material.

3. The method of claim 1, wherein causing comprises:
    selecting a first thickness of the first material and a second thickness of the second material such that the first amount of time will be substantially equal to the second amount of time.

4. The method of claim 1, wherein causing comprises:
    adding a delay line such that the first amount of time will be substantially equal to the second amount of time.

5. The method of claim 1, wherein the first wave is a reflected wave and the second wave is a transmitted wave.

6. The method of claim 1, wherein the first material is a composite and the second material is a metal.

7. The method of claim 2 further comprising:
    measuring the vibrations on the first end of the first material.

8. The method of claim 7 further comprising:
    identifying a break of the bond interface using the vibrations measured on the first end of the first material.

9. The method of claim 1 further comprising:
    identifying a break of the bond interface using a non-destructive method for bond inspection.

10. A method for testing bond interface strength, the method comprising:
    transmitting an initial wave into a first end of a first material connected to a second material by an adhesive at a bond interface such that the initial wave splits into a first wave and a second wave at the bond interface;

transmitting a second initial wave into a second end of the second material such that the second initial wave splits into a third wave and a fourth wave at the bond interface; and causing the first wave to travel through the first material to the first end of the first material and back to the bond interface in a first amount of time and the fourth wave to travel through the first material in a fourth amount of time, such that the first amount of time is substantially equal to the third amount of time, wherein the first material is dissimilar to the second material, and wherein a tension is obtained in the adhesive at the bond interface.

11. The method of claim 10, further comprising:
repeatedly transmitting additional waves into the first material to generate vibrations in the first material and the second material.

12. The method of claim 10, wherein causing comprises:
transmitting the initial wave and the second initial wave at different times such that the first amount of time is substantially equal to the fourth amount of time.

13. The method of claim 10, wherein causing comprises:
adding a delay line to at least one of the first material and the second material such that the first amount of time is substantially equal to the fourth amount of time.

14. The method of claim 10, wherein the first wave is a reflected wave, the second wave is a transmitted wave, the third wave is a reflected wave, and the fourth wave is a transmitted wave.

15. The method of claim 10, wherein the first material is a composite and the second material is a metal.

16. The method of claim 11 further comprising:
measuring the vibrations on the first end of the first material.

17. The method of claim 16 further comprising:
identifying a break of the bond interface using the vibrations measured on the first end of the first material.

18. An apparatus comprising:
a number of lasers configured to generate a number of waves in a first material and a second material; and
a controller associated with the number of lasers configured to control the number of lasers to generate an initial wave of the number of waves, transmit the initial wave into a first end of a first material such that the initial wave splits into a first wave and a second wave at a bond interface bonding the first material to the second material with an adhesive,
wherein the first wave travels through the first material to the first end of the first material and back to the bond interface in a first amount of time and the second wave travels through the second material to a second end of the second material and back to the bond interface in a second amount of time, wherein the first material is dissimilar to the second material, and wherein the first amount of time is substantially equal to the second amount of time.

19. The apparatus of claim 18, wherein a first thickness of the first material and a second thickness of the second material are selected such that the first amount of time is substantially equal to the second amount of time.

20. The method of claim 1, wherein delay lines on at least one of the first material and the second material allow the first amount of time to be substantially equal to the second amount of time.

* * * * *